United States Patent [19]

Jessel, Jr. et al.

[11] Plant 4,562

[45] Jul. 1, 1980

[54] CHRYSANTHEMUM PLANT

[75] Inventors: Walter H. Jessel, Jr., Grantsville, W. Va.; William E. Duffett, Salinas, Calif.

[73] Assignee: Yoder Brothers, Inc., Barberton, Ohio

[21] Appl. No.: 10,851

[22] Filed: Feb. 9, 1979

[51] Int. Cl.[2] ..... A01H 5/00

[52] U.S. Cl. ..... Plt./76

[58] Field of Search ..... Plt./76

*Primary Examiner*—Robert E. Bagwill

*Attorney, Agent, or Firm*—Donald D. Jeffery

[57] ABSTRACT

A chrysanthemum plant known by the cultivar name Capri and particularly characterized as to uniqueness by the combined characteristics of semi-incurved capitulum form; decorative capitulum type; dark lavender pink ray floret color; diameter across face of capitulum ranging from 100 to 120 mm. at maturity; uniform nine week photoperiodic flowering response to short days; medium plant height when grown as a pinched spray pot, and semi-spreading branching pattern.

7 Drawing Figures

The present invention comprises a new and distinct cultivar of *Chrysanthemum morifolium*, Ramat., hereinafter referred to by the cultivar name Capri.

Capri is a product of a planned breeding program which had the objective of creating new chrysanthemum cultivars with decorative capitulum type, with lavender ray floret color, with eight or nine week flowering response, and with the ability to produce commercially acceptable quality in year round pot mum programs. Such traits in combination were not present in previously available commercial cultivars.

Capri was originated from a cross made in a controlled breeding program in Barberton, Ohio in 1974. The female parent was #70048004 (unnamed seedling), a yellow decorative originated by the present inventors from a cross between Mandalay (unpatented; commercially available) and Sunstar (unpatented; commercially available). The male parent of Capri was Royal Purple (unpatented; commercially available), a lavender decorative of parentage unknown to the present inventors. Mandalay and Sunstar are products of the breeding program of the present inventors.

Capri was discovered and selected as one flowering plant within the progeny of the stated cross by Walter H. Jessel, Jr. and William E. Duffett on Dec. 3, 1975 in a controlled environment in Barberton, Ohio.

The first act of asexual reproduction of Capri was accomplished when vegetative cuttings were taken from the initial selection in February, 1976 in a controlled environment in Barberton, Ohio, by a technician working under formulations established and supervised by Walter H. Jessel, Jr. and William E. Duffett. Horticultural examination of selected units initiated Oct. 20, 1976 has demonstrated that the combination of characteristics as herein disclosed for Capri are firmly fixed and are retained through successive generations of asexual reproduction.

Capri has not been observed under all possible environmental conditions. The phenotype may vary significantly with variations in environment such as temperature, light intensity, and daylength. The following observations, measurements, and comparisons describe plants grown in Barberton, Ohio and in Salinas, Calif. under greenhouse conditions which approximate those generally used in commercial practice.

The following traits have been repeatedly observed and are determined to be basic characteristics of Capri which in combination distinguish this chrysanthemum as a new and distinct cultivar:

(1) Semi-incurved capitulum form.

(2) Decorative capitulum type.

(3) Dark lavender pink ray floret color, with minimal color oxidation.

(4) Diameter across face of capitulum ranging from 100 to 120 mm. at maturity.

(5) Uniform nine week photoperiodic flowering response to short days.

(6) Medium plant height (requiring 1–2 long day weeks prior to pinch and short days, and one application of 2500 ppm B-9 SP 14 to 21 days after the beginning of short days to attain a flowered plant height of 30 to 45 cm).

(7) Semi-spreading branching pattern.

The accompanying photographic drawings show typical inflorescence and foliage characteristics of Capri, with colors being nearly as true as possible with illustrations of this type. Sheet 1 is a color photograph of the inflorescence of Capri. Sheet 2 is a black and white photograph showing three views of the capitulum of Capri. Sheet 3 shows typical foliage characteristics of Capri at three stages of growth.

Of the many commercial cultivars known to the present inventors, the most similar existing cultivars in comparison to Capri are the cultivars Royal Trophy, (disclosed in U.S. Plant Pat. No. 3,549), and the parental cultivar Royal Purple. Reference is made to attached Chart A which compares certain characteristics of Capri to those same characteristics of Royal Trophy and Royal Purple. General comparisons are as follows:

(1) In comparison to Royal Trophy, Capri has less blue ray floret color, more incurved flower form, more spreading branching pattern, and smaller diameter across face of capitulum. The capitulum type, plant height, and flowering response period of Capri are similar to those same characteristics of Royal Trophy.

(2) In comparison to Royal Purple, Capri has more spreading branching pattern, and shorter plant height. The ray floret color, capitulum form, capitulum type, diameter across face of capitulum, and flowering response period of Capri are similar to those same characteristics of Royal Purple.

In the following description, color references are made to the Royal Horticultural Society Colour Chart. The color values were determined between 11:00 and 11:30 A.M. on Nov. 2, 1978 under 100 foot-candle light intensity at Salinas, Calif.

Botanical classification: *Chrysanthemum morifolium,* Ramat., cv Capri.

INFLORESCENCE

A. Capitulum

*Form.*—Semi-incurve.

*Type.*—Decorative.

*Diameter across face.*—100 to 120 mm.

B. Corolla of ray florets:

*Color (abaxial).*—72-A streaked lightly over 78-D.

*Color (adaxial).*—78-D to 78-C.

*Persistence.*—Resists shatter.

C. Reproductive organs:

*Androecium.*—Present disc florets only; scant to few; scant pollen.

*Gynoecium.*—Present both ray and disc florets.

PLANT

A. General appearance: Semi-spreading branching pattern; medium height.

B. Foliage:

*Color (abaxial).*—Approximately 137-A.

*Color (adaxial).*—Approximately 138-A to 138-B.

CHART A

COMPARISON OF CAPRI, ROYAL TROPHY AND ROYAL PURPLE

| CULTIVAR | RAY FLORET COLOR | CAPITULUM FORM AND TYPE | BRANCHING PATTERN |
|---|---|---|---|
| Capri | Dark Lavender Pink | Semi-incurved Decorative | Semi-spreading |
| Royal Trophy | Dark Lavender | Flat Decorative | Semi-upright |
| Royal Purple | Dark Lavender Pink | Semi-incurved Decorative | Semi-upright |

| CULTIVAR | DIAMETER ACROSS FACE OF CAPITULUM | PLANT HEIGHT | FLOWERING RESPONSE PERIOD |
|---|---|---|---|
| Capri | 100 to 120 mm. | Medium | 9 week |
| Royal Trophy | 110 to 130 mm. | Medium | 9 week |
| Royal Purple | 100 to 120 mm. | Tall | 9 week |

COMPARISONS MADE OF PLANTS GROWN AS PINCHED DISBUDDED POTS IN BARBERTON, OHIO AND IN SALINAS, CALIFORNIA.

We claim:

1. A new and distinct cultivar of *Chrysanthemum morifolium,* Ramat., plant as shown and described, known by the cultivar name Capri and particularly characterized as to uniqueness by the combined characteristics of semi-incurved capitulum form; decorative capitulum type; dark lavender pink ray floret color, with minimal color oxidation; diameter across face of capitulum ranging from 100 to 120 mm. at maturity; uniform nine week flowering response; medium plant height, and semi-spreading branching pattern.

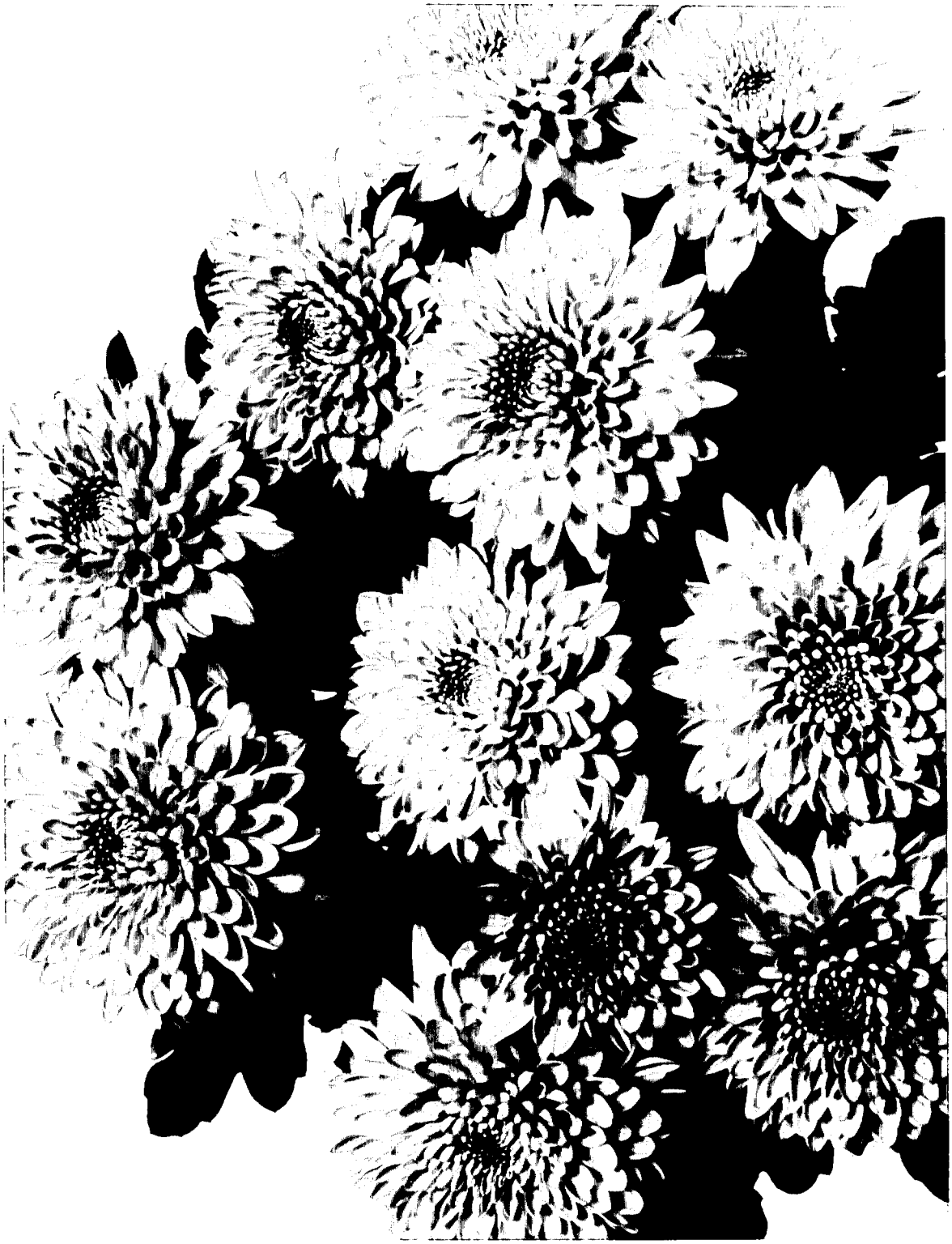

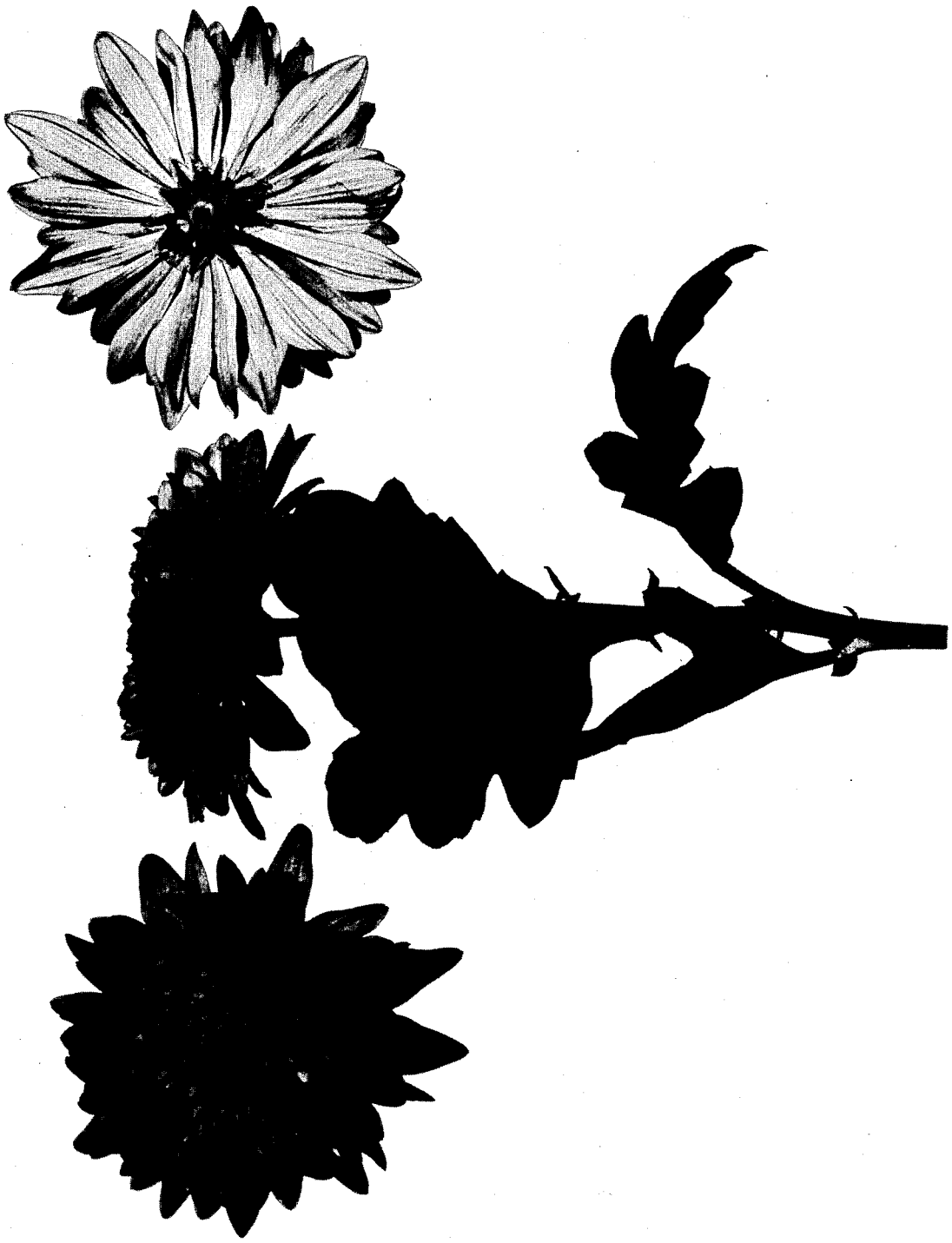

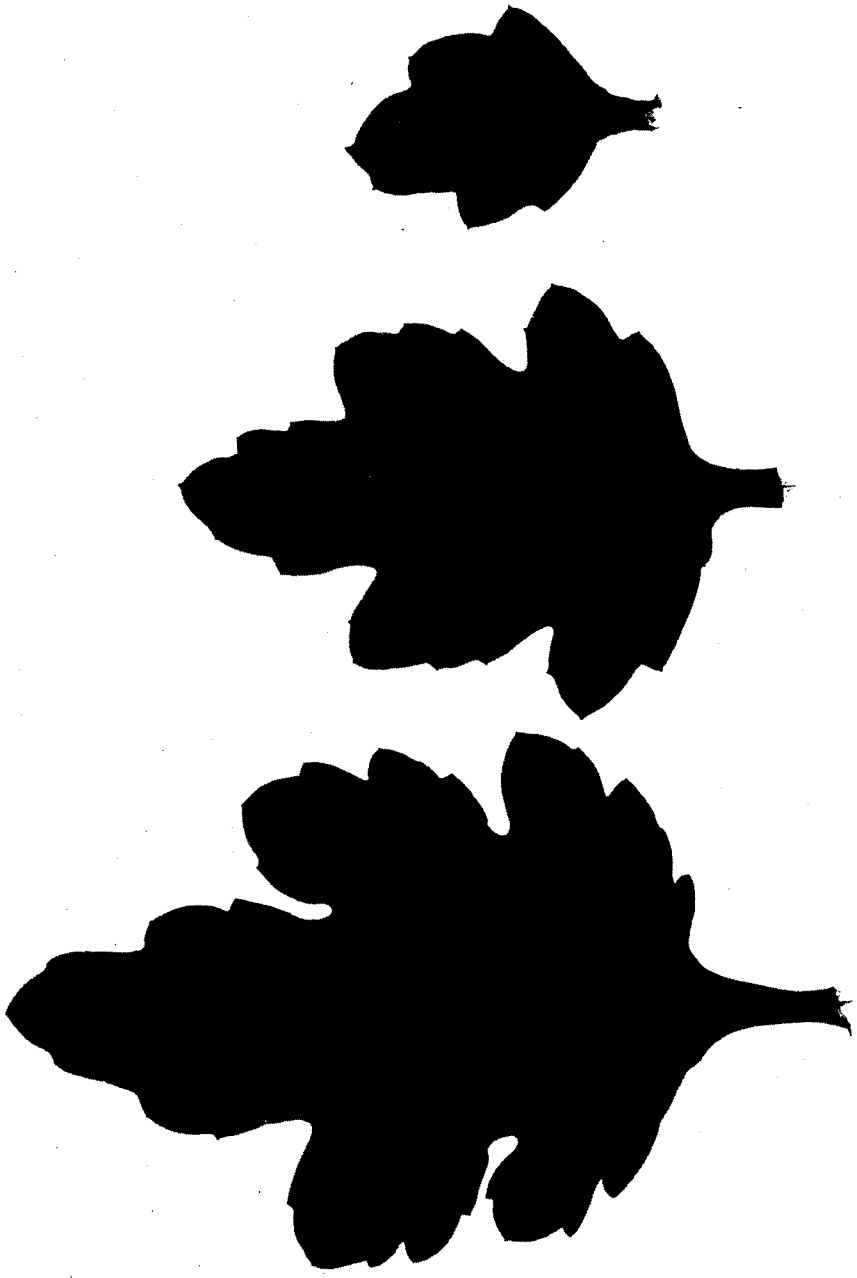

* * * * *